United States Patent

LeMay

[11] 4,002,910
[45] Jan. 11, 1977

[54] RADIOLOGY

[75] Inventor: Christopher Archibald Gordon LeMay, Osterley, England

[73] Assignee: E M I Limited, Hayes, England

[22] Filed: July 17, 1975

[21] Appl. No.: 596,623

[30] Foreign Application Priority Data
July 20, 1974 United Kingdom ............ 32257/74

[52] U.S. Cl. .......................... 250/360; 250/445 T; 250/460
[51] Int. Cl.$^2$ ........................................ G01M 23/00
[58] Field of Search .......... 250/362, 363, 366, 360, 250/445, 460

[56] References Cited
UNITED STATES PATENTS
3,778,614  12/1973  Hounsfield ..................... 250/362

Primary Examiner—Harold A. Dixon
Attorney, Agent, or Firm—Fleit & Jacobson

[57] ABSTRACT

In a method of constructing a representation of the distribution of absorption in a planar region of a body interpolation is provided, between data signals representing absorption of radiation along parallel paths, to provide signals for an increased number of such paths as required for the processing used. The interpolation is performed by forming differences of second or higher order, subdividing the differences and then combining them by running additions.

5 Claims, 5 Drawing Figures

RADIOLOGY

The present invention relates to a method of constructing a representation of the distribution of absorption with position in a planar region of a body.

In U.S. Pat. No. 3,778,614 there is described apparatus of that type including a source of penetrating radiation and detector means responsive to the radiation. The source and detector means are scanned, in the plane of the slice and relative to the body, so that the detector means provides output signals indicative of the absorption suffered by the radiation as it transverses many different paths through the body in the said plane. The radiation beam paths are grouped in sets of parallel paths, such as that indicated in FIG. 1 by dashed lines representing the centrelines of the paths, each set being at a different angle relative to the body. The paths of each set do not need to be strictly parallel but should not deviate too much from parralelism. In the said U.S. Pat. the data signals relating to each of the beam paths are processed by a method of successive approximations. The final representation is thus built up in a final so-called matrix store in addresses corresponding to the centre points of meshes of a notional cartesion meshwork, regarded as lying in the said planar region. Such a meshwork has also been shown in FIG. 1 superimposed on the illustrative parallel set of beam paths. It should be understood, however, that many more beam paths and mesh elements would be used in practise.

An alternative form of processing is described in U.S. Pat. No. 3,924,129. In that method, which is of a convolution character, the data appropriate to the beam paths of a parallel set are first processed to allow the image to be formed in a so-called layergram manner. After such convolution an accurate image is formed by summing in each store address the convolved data values, $f_1$, $f_2$ etc. for all beam paths, one from each parallel set, whose centrelines pass through or close to the appropriate mesh centre point. Unfortunately, although the beam paths may all pass through mesh centre points for one orientation of the scan, that is not generally true for all scanning angles as can be seen from FIG. 1. The set shown, inclined at angle $\theta$ to the vertical of the mesh, comprises ten beams, spaced along the axis of a set parameter r in a direction perpendicular to the beams. The appropriate convolved data values are shown as $f_1$ to $f_{10}$. It can be seen that the third beam from the left, associated with datum $f_3$, passes through a centre point at $a$ so that the datum $f_3$ may be applied to the address for that mesh. However the beam misses a centre point at $b$ by a distance $x$ which is less than the beam centreline spacing so that there is no datum for mesh $b$.

To provide data for each such mesh it is necessary to interpolate between the available data to provide, for example, thrity interpolated beam absorption values between each derived pair such as $f_3$ and $f_4$. Thus one interpolated or derived beam path will pass through each mesh centre point or sufficiently close for the absorption value to be allocated to that point without significant error.

Figure 1:
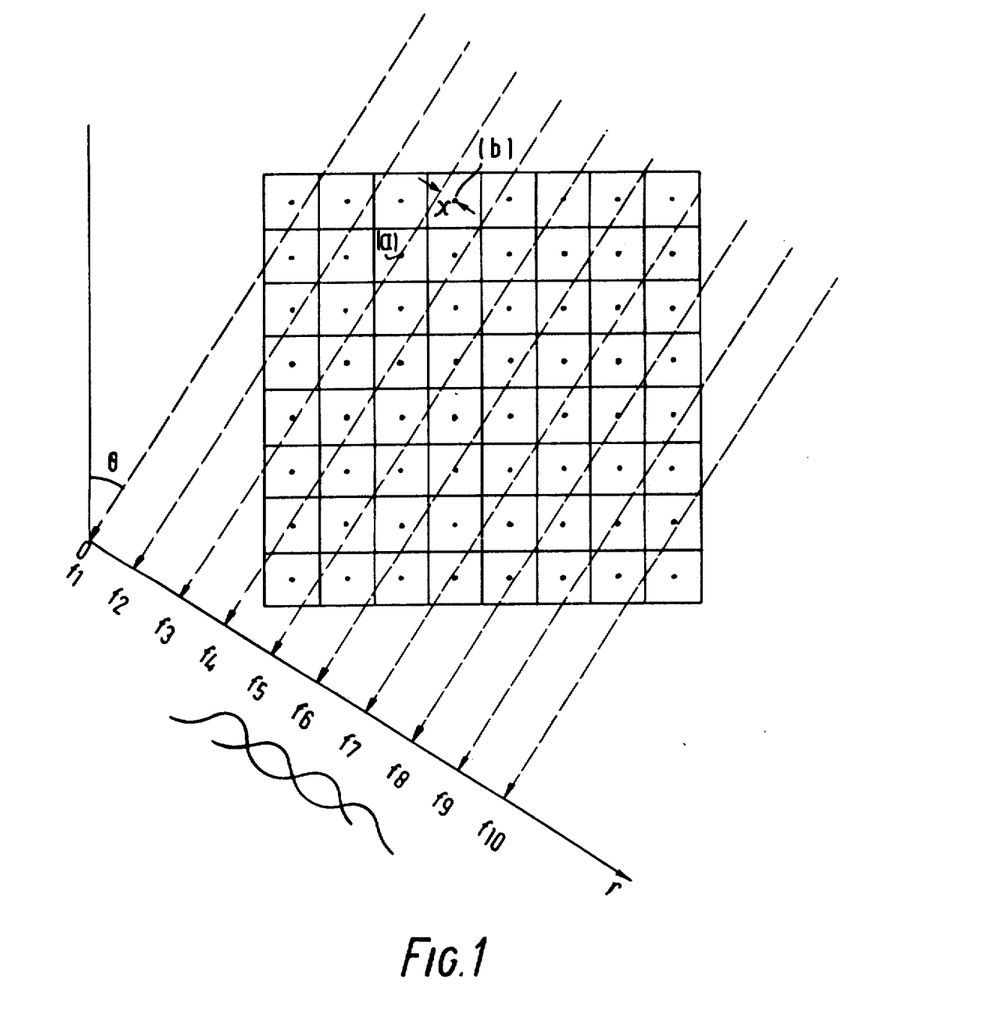
FIG. 1 has the significance explained hereinbefore.

As a result partly of the distribution of radiation imposed on the beams by collimator means, employed to define the beams, and partly of the continuous motion of the beam during scanning, each beam tends to have a sinusoidal distribution of intensity. This may extend skirt-to-skirt over a range equal to twice the spacing of the beam paths, i.e. twice the sampling interval, as shown in FIG. 1 for some of the paths illustrated. It may, however, in some circumstances extend over two or more of the adjacent beam paths.

Interpolation has been performed in terms of that effective sinusoidal distribution of the contributing beams. In that case, a proportion of the absorption suffered by one of these two beams contributes to the mesh point absorption value according to a sinusoidal function of the displacement of the beam from that point. A complementary proportion of the absorption suffered by the other of the two beams also contributes to this value. This type of interpolation is accurate in the sense that a uniform field of original absorption yields on interpolation, as it should, a uniform pattern of absorption in the final reconstruction. The method however fully reflects statistical errors of data measurement into this reconstruction. This is in contrast with the fact that at the frequency of such measurement, namely the sampling rate, the response of the system as a whole, following recognised sampling principles, is zero in regard to true information.

It is an object of the present invention to provide an improved method of reconstruction with a reduced response to such statistical errors.

It is another object of the invention to provide a method of reconstruction capable of relatively more rapid operation.

According to the present invention there is provided a method of constructing a representation of the distribution of absorption in a planar region of a body including the steps of providing data signals representing the absorption of the radiation along a plurality of substantially parallel paths in the plane of the said region, interpoling between the said data signals to provide further data signals representing the absorption of the radiation along an increased number of such paths and allocating, to each of a plurality of predetermined points in a field notionally delineated in the said region, the data signal or further data signal associated with the paths whose centreline passes closest to that point, wherein the interpolation is achieved by forming signals representing differences of said data extending to order $m$, where $m$ is at least two, subdividing some of said difference signals and combining the subdivided differences by running addition.

In order that the invention may be better understood it will now be described by way of example with reference to the accompanying drawings in which.

Figure 2:
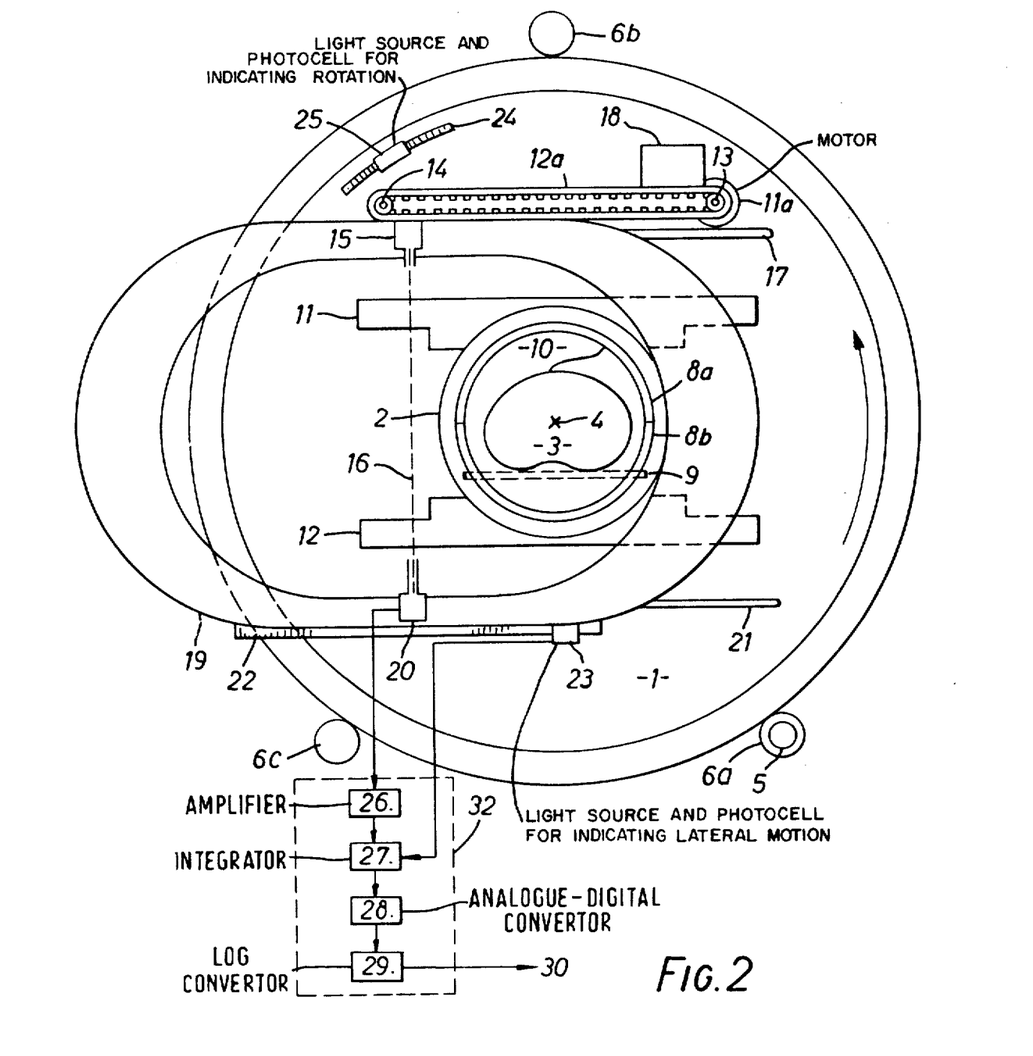
FIG. 2 shows a typical X-ray apparatus as referred to hereinbefore.

Referring now to FIG. 2 there is shown in end elevation an X-ray apparatus of the type described and in conjunction with which the invention is employed. A turntable 1, having a central aperture 2, in which a body 3 is to be examined is inserted, is arranged so as to be capable of rotation about an axis 4 perpendicular to its plane and centrally disposed in the aperture. The turntable is rotated by motor 5 which drives a gear wheel 6a, the wheel 6a being arranged to engage cogs formed around the periphery 7 of the turntable 1. The gear wheel 6a is journalled in a fixed main frame of the apparatus, not shown, and the turntable is further supported by two undriven gear wheels 6b and 6c also journalled in the main frame.

The body 3 remains fixed while the turntable 1 rotates about it. A two part ring member 8a and 8b is fitted around the region of the body 3 to be examined and the ring is secured to a patient supporting structure which comprises a two part bed, one part on either side of the turntable so as to hold the patient securely in position such that the exploring radiation can transverse the region of interest. Only one part of the supporting structure 9 is shown in the drawing for the sake of clarity. Disposed around the patient in the region of interest and trapped in position by the ring 8a, 8b is a material 10, for example water in a bag, which absorbs the radiation to an extent similar to body tissue. The material 10 helps to exclude air from the region around the body and also assits in the accommodation of patients of differing sizes, since the apparatus treats the entire content of the ring 8a, 8b as being a body.

The turntable 1 carries two compensating members 11 and 12 fixed thereto. These members are arranged to provide a substantially uniform absorption to the radiation for all beam paths of a lateral scan despite the circular cross section of the "body" of ring 8a, 8b. Thus it is ensured that any variations of absorption are caused substantially only by variations in the body 3.

Also fixedly secured to the turntable 1 is a reversible motor 11a which drives a toothed belt 12a by means of a drive shaft 13 journalled in turntable 1. The belt 12a also passes over an idler wheel 14 also journalled in turntable 1. Secured to the belt 12a is a source 15 of a single beam of radiation 16, in this example, although it may also be a fan shaped swath as described in U.S. Pat. No. 3,946,234. The source is driven to and fro laterally by belt 12a, being mounted on a bearing travelling on a track 17. A counter balance weight 18 is fixed to the opposite side of belt 12a to compensate for out of balance forces during the lateral movement.

Linked to the source 15 by a light weight but rigid yoke 19 is a collimator/detector unit 20 which may contain, for example, a scintillator crystal and photomultiplier. In the event that the source 15 provides a fan shaped swath of radiation, the detector unit 20 comprises a plurality of such crystals and photomultipliers, defining a plurality of beam paths in the fan, as described in aforesaid application Ser. No. 502,080. The detector unit 20 also moves on a bearing on track 21 on turntable 1. Yoke 19 carries a graticule 22 which cooperates with a light source and photocell 23 to provide signals indicative of the process of the lateral scan. The graticule 22 is a translucent strip carrying engraved lines which interrupt the light path between the light source and the photcell. The signals obtained are used by a computer controlling the processing to determine the position of the beam 16 in relation to the body 3 for each data value obtained by detector 20. A similar graticule 24 fixed to turntable 1 and combined with a light source and photocell unit 25, fixed in a manner not shown to the main frame of the apparatus, indicates the progress of the rotational movement for the same purpose. The apparatus is arranged to make a lateral traverse to provide one parallel set of data as shown in FIG. 1 and to then make an orbital movement so as to repeat the lateral movement at a different inclination. This process is repeated over, say, 180° of rotation to build up the desired number of parallel sets.

The signals from detector unit 20 are amplified by an amplifier 26 and integrated in an integrator 27 over a period determined by successive pulses from photocell 23. After further processing by analogue-to-digital converter 28 and log converter 29 they are transferred at 30 to a computer for processing as described in the said U.S. Pat. 3,924,129. Units 26 to 29 which operate as described in the said U.S. Pat. No. 3,924,129 or in the aforementioned U.S. Pat. No. 3,778,614 may be said to comprise an inital processor indicated by reference numeral 32.

It will be understood that the invention is not restricted to use with an X-ray apparatus of the type described but may be used with any other apparatus providing data which requires such interpolation. Other such apparatus are those described in U.S. Pat. No. 3,937,963 or U.S. Application Ser. No. 544,799 filed Jan. 28, 1975, in which the parallel sets of data are assembled from data received from a fan shaped spread of beam not subjected to a tranverse scanning movement.

Figure 3:
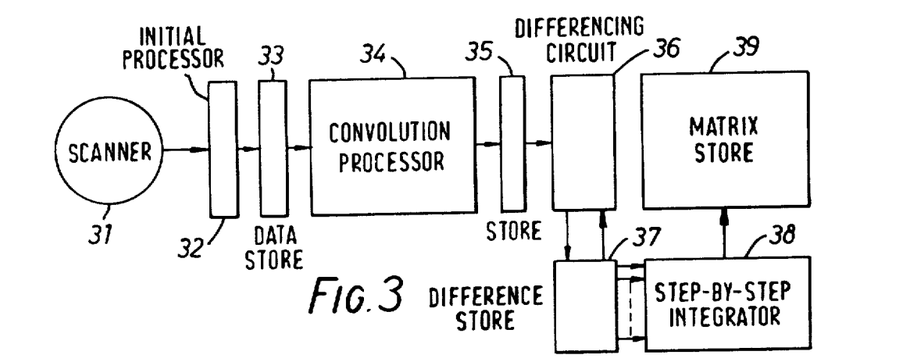
FIG. 3 shows in block diagrammatic form a circuit in accordance with the invention.

FIG. 3 shows, in block schematic form, a circuit for carrying out image reconstruction. Reference 31 signifies the X-ray apparatus described in relation to FIG. 2 and reference 32 is in the initial processor also described. Absorption data derived from the scanner 31 are transferred via the initial processor 32 to a data store 33 for storage in the form of parallel sets.

For the purpose of construction of the representation of linear absorption of the region examined, the data signals are withdrawn, parallel set by parallel, from store 33 and processed by a convolution processor 34. Forms which this processor may take are indicated and described in detail in the specifications of U.S. Pat. No. 3,924,129 and U.S. application Ser. No. 544,796 filed Jan. 28, 1975 to achieve the result described hereinbefore. As each parallel set is processed the so-transformed data signals are stored in a manner also described the said specifications, in a storage means shown at 35 in FIG. 3.

Following the invention a differencing circuit 36 withdraws the stored data held in store 35 for each parallel set in turn, and forms first and higher order differences of the data values of the set, transferring them to a difference store 37. The details of this differencing will be more fully explained subsequently. In a manner also to be explained more fully, the difference values stored in store 37 are withdrawn for each parallel set in turn by an intergrator circuit 38. This circuit performs a functional integration in step-by-step manner in the intervals between differenced values so as to derive absorption values appropriate to be stored at the addresses of matrix store 39. The nature of this store the function of which was described hereinbefore is also set out more fully in the said U.S. application Ser. No. 544,796. As will become apparent the integration process tends to exercise a smoothing effect upon the functional values distributed to the matrix store 39, so improving the discrimination of the apparatus against statistical fluctuation in the original acquisition of data. The circuits 33 to 39 are represented in block form since in practice are provided by a digital computer including storage facilities, the computer being programmed to carry out the functional operations about to be described in more detail to the extent that they have not already been indicated.

Referring to the action of the differencing circuit 36, as described hereinbefore the convolved parallel set values relative to a particular set, as stored in store 5, are represented in order as $$f_1, f_2, f_3, \ldots, f_k, \ldots, f_N$$

at increasing values of $r$. The $k$th first order difference of this series, represented as $\Delta_k^1$ is defined by $$\Delta_k^1 = f_{k+1} - f_k$$

The circuit 36 forms all the differences of the series $$\Delta_1^1, \Delta_2^1, \Delta_3^1, \ldots, \Delta_k^1, \ldots, \Delta_{N-1}^1$$

The $k$th difference of the second order, namely $\Delta_k^2$, is defined by $$\Delta_k^2 = \Delta_{k+1}^1 - \Delta_k^1$$

and the circuit 36 also forms all the differences of the series $$\Delta_1^2, \Delta_2^2, \Delta_3^2, \ldots, \Delta_k^2, \ldots, \Delta_{N-2}^2.$$

All these differences and, if desired, similar defined differences of higher order are stored, as they are formed, in the difference store 37 in locations determined by the programme.

The character of the integrative interpolation performed by the integrator circuit 38 on such differences will now be discussed for a simple example. Thus suppose the transformed data of a parallel set as withdrawn from the store 35 to consist solely of five values $f_1, f_2, f_3, f_4, f_5$, equal respectively to the magnitudes $$0,0,1,0,0$$

These valves relate to equally spaced values, of the set parameter $r$.

According to the expressions given hereinbefore it will be seen that the first order differences are given by $$\Delta_1^1 = 0,$$
$$\Delta_2^1 = 1,$$
$$\Delta_3^1 = -1$$

and $$\Delta_4^1 = 0,$$

TABLE 1

| Set Parameter $r$ | Original function $f$ | Original first order difference $\Delta_k^1$ | Original second order difference $\Delta_k^2$ | Subdivided second order difference $\Delta_k^2/n^2 = \Delta_p^{2*}$ | Reconstructed first order difference $\Delta_p^{1*}$ | Reconstructed function valves $\phi(r)$ |
|---|---|---|---|---|---|---|
| 0 | $f_1 = 0$ | | | 0 | 0 | |
| 0.1 | | | | | | |
| 0.2 | | | | | 0 | |
| 0.3 | | | | | | |
| 0.4 | | | | | 0 | |
| h/2 = | | | | | | |
| 0.5 | | 0 | | | | 0 |
| 0.6 | | | | 1/25 | | 0 |
| 0.7 | | | | | 1/25 | |
| 0.8 | | | | 1/25 | | 1/25 |
| 0.9 | | | | | 2/25 | |
| h = | | | | | | |
| 1.0 | $f_2 = 0$ | | | 1/25 | | 3/25 |
| 1.1 | | | | | 3/25 | |
| 1.2 | | | | 1/25 | | 6/25 |
| 1.3 | | | | | 4/25 | |
| 1.4 | | | | 1/25 | | 10/25 |
| 3h/2 = | | | | | | |
| 1.5 | | 1 | | | 5/25 | |
| 1.6 | | | | −2/25 | | 15/25 |
| 1.7 | | | | | 3/25 | |
| 1.8 | | | | −2/25 | | 18/25 |
| 1.9 | | | | | 1/25 | |
| 2h = | | | | | | |
| 2.0 | $f_3 = 1$ | | −2 | −2/25 | | 19/25 |
| 2.1 | | | | | −1/25 | |
| 2.2 | | | | −2/25 | | 18/25 |
| 2.3 | | | | | −3/25 | |
| 2.4 | | | | −2/25 | | 15/25 |
| 5h/2 = | | | | | | |
| 2.5 | | −1 | | | −5/25 | |
| 2.6 | | | | 1/25 | | 10/25 |
| 2.7 | | | | | −4/25 | |
| 2.8 | | | | 1/25 | | 6/25 |
| 2.9 | | | | | −3/25 | |
| 3h = | | | | | | |
| 3.0 | $f_4 = 0$ | | 1 | 1/25 | | 3/25 |
| 3.1 | | | | | −2/25 | |
| 3.2 | | | | 1/25 | | 1/25 |
| 3.3 | | | | | −1/25 | |
| 3.4 | | | | 1/25 | | 0 |
| 7h/2 = | | | | | | |
| 3.5 | | 0 | | | 0 | |

TABLE 1-continued

| Set Parameter r | Original function f | Original first order difference $\Delta_k^1$ | Original second order difference $\Delta_k^2$ | Subdivided second order difference $\Delta_k^2/n^2 = \Delta_p^{2*}$ | Reconstructed first order difference $\Delta_p^{1*}$ | Reconstructed function valves $\phi(r)$ |
|---|---|---|---|---|---|---|
| 3.6 | | | | 0 | | |
| 3.7 | | | | | | |
| 3.8 | | | | 0 | | |
| 3.9 | | | | | | |
| 4h = | | | | | | |
| 4.0 | $f_5 = 0$ | | 0 | 0 | | | and the second order differences are given by $$\Delta_1^2 = 1$$

$$\Delta_2^2 = -2$$

and $$\Delta_3^2 = 1$$

As mentioned hereinbefore higher order differences may be similarly derived and interpolated values may be formed from many combinations of such differences other than first order differences only. In this example, however, formations of interpolated values from only the second order differences will be described according to the preferred embodiment of the invention.

The initial function is rebuilt from intermediate values of $r$ from the second order differences alone; Therefore, in order to provide the necessary interpolated values, these differences are subdivided into $n$ equal values, where $1/n$ is the value of the spacing of the increased number of function values to the signal number of such values. Since second order differences are used, each subdivided difference is $1/n^2$ of the corresponding original difference if the reconstructed function is to be correct. In a practical example $n$ may have a value of thirty or forty depending on the number of interpolated values required. However in this simplified example $n$ will be given the value five. The reconstruction of the function is thus as shown in Table 1 in which the differences have been shown in relation to values of the set variable $r$. The signficance of the parameter $h$ will be explained hereinbefore.

It will be seen that a more closely spaced set of second order differences has been provided, there being in this example five for each span of the set parameter $r$ associated with one of the original second order differences. The subdivided differences have been indicated by $\Delta_p^{2*}$ where each value of $\Delta_p^{2*}$ is equal to a value of $\Delta_k^2/n^2$. It should be understood that $p$ indicates the $p^{th}$ difference in the set from an initial value and does not directly relate to value of $r$. The value of $\Delta_{p-1}^{2*}$ could be taken to be the zero value at $r=0$, however it is more convenient to set $\Delta_{p-1}^{2*}$ at the first non-zero value, at $r=0.6$ in this example.

Using the values of $\Delta_p^{2*}$ a more closely spaced set of first order differences $\Delta_p^{1*}$ are constructed by the reverse of the relation given above i.e.

$$\Delta_{p+1}^{1*} = \Delta_p^{1*} + \Delta_p^{2*}$$

The construction of this set of $\Delta_p^{1*}$ is achieved by a running addition starting from an initial value of $\Delta_{p-1}^{1*}$ which is zero at a known position, namely that of $r=0.5$ in this example.

Similarly the new first order differences are used to construct a new more closely spaced set of function values $\phi(r)$ by a similar running addition from a zero starting value at the value $r$ associated with $\Delta_{p-1}^{2*}$. It will be seen that the newly constructed function comprises an increased number of more closely spaced values correspondingly running smoothly among the original values, through not necessarily passing through them.

Comparing Table 1 with FIG. 1 it can be seen that a value of the function for mesh point $b$ between values $f_3$ and $f_4$ may be more accurately obtained. Assuming $x$ to be 0.4, on the scale of $r$ given, the respective value would be $\phi_{(2,4)}=3/5$ for the 0,0,1,0,0, function of the table.

The reconstruction can also be based on a series of running additions based on third or higher order differences. In general reconstruction from m'th order differences requires $m$ such recurrent additions. However a single recurrent addition from first order differences will give a discontinuous reconstructed function.

As mentioned hereinabove, the integration may be based on such running addition using combinations of such differences, including the first order differences. A further example will be given to illustrate that alternative approach and furthermore, to more properly indicate the nature of the process involved, the relationships used will be explained in terms of finely divided steps approximately to continuous integration. The function generated by the integration will be represented as before by $\phi(r)$, and the equal spacing between original function valves $f$ will be denoted by $h$.

In the range of $r$ lying between $\frac{1}{2}h$ and $3/2h$ the function $\phi(r)$, denoted in this range by $\phi_1(r)$, is defined according to $$\phi_1(r) = \frac{1}{h} \int_o^u \Delta_1^2 dt + \frac{1}{h^2} \int_o^u \int_o^{t'} \Delta_1^2 dt' dt.$$

Where $u$ is the difference between a value of the set variable $r$ and at least value of $r$ in the range and $t$ and $t'$ are similarly variables on the scale of $r$.

In the range $3/2h$ to $5/2h$ the definition is correspondingly $$\phi_2(r) = \phi_1\left(\frac{3}{2}h\right) + \frac{1}{h}\int_0^u \Delta_2^1 dt + \frac{1}{h^2}\int_0^u \int_0^t \Delta_2^2 dt' dt,$$

and in the range $5/2h$ to $7/2h$ the definition in like character is $$\phi_3(r) = \phi_2\left(\frac{5}{2}h\right) + \frac{1}{h}\int_0^u \Delta_3^1 dt + \frac{1}{h^2}\int_0^u \int_0^t \Delta_3^2 dt' dt.$$

It should be understood that these expressions have been arbitrarily derived to achieve the desired interpolation. Many similar expressions may be derived according to the general principles of the invention, namely to achieve a smooth interpolation by recurrent addition.

In these expressions the first and second order differences will have the values given above if the function is the 0,0,1,0,0 function as used in the previous example.

It follows in that case from the three expressions given that $$\phi_1(r) = \frac{1}{2} \cdot \frac{u^2}{h^2},$$

$$\phi_2(r) = \frac{1}{2} + \frac{u}{u} - \frac{u^2}{h^2},$$

$$\phi_3(r) = \frac{1}{2} - \frac{u}{h} + \frac{1}{2} \cdot \frac{u^2}{h^2},$$

and substituting its appropriate values of $h$ and $u$ $\phi(\frac{1}{2}h) = 0$, $\phi(h) = \frac{1}{4}$, $\phi(3/2h) = \frac{1}{2}$, $\phi(2h) = \frac{3}{4}$, $\phi(5/2h) = \frac{1}{2}$, $\phi(3h) = \frac{1}{4}$, $\phi(7/2h) = 0$.

Figure 4:
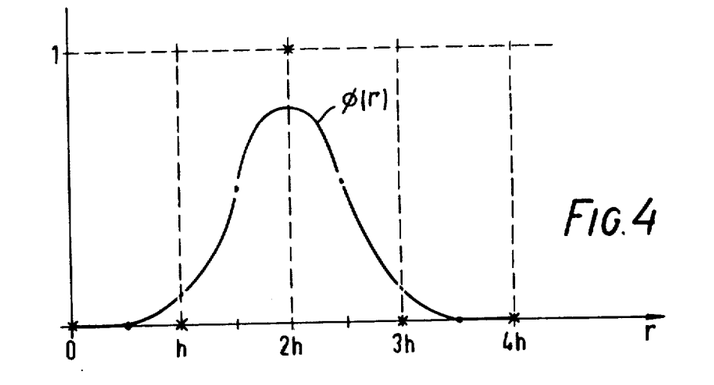
FIGS. 4 and 5 are graphs showing the character of the interpolation according to the invention.

In the ranges 0 to $\frac{1}{2}h$ and $7/2h$ to $4h$ the value of $\phi(r)$ is zero. FIG. 4 gives the plot of the function over the total range 0 to $4h$. It will be seen that the function represents a smooth curve which apart from the initial and final values of the assumed data does not pass through the data points but purses a path lying between them. Thus the interpolation technique of the invention tends to smooth the basic data, and to this extent it reduces the response of the system to statistical fluctuations in the data, which the sinusoidal technique referred to does not. On the other hand the technique of the invention allows a more complete response at the higher frequencies to true image information than does the sinusoidal method. It will be observed that the two examples given for the same initial function give similar results.

It practice, as stated, the integrator 38 operates on a basis of recurrent addition, rather than continuous integration, so that the integrals in the second example given are formed as running summations in finite steps. Correspondingly the differential $dt$ has to be replaced by the finite difference. $\Delta t$, which is chosen so that $$n \cdot \Delta t = h$$

in which $n$ is taken to be an integer as before. First order integrals such as $$\int_0^u \frac{\Delta^1}{h} dt$$

thus becomes replaced by single summations of the character $$\sum_0^x \frac{\Delta^1}{n},$$

and in the same kind of way the second order integral $$\int_0^u \int_0^t \frac{\Delta^2}{h^2} dt' dt$$

becomes the double summation $$\sum_0^x \left( \sum_0^t \frac{\Delta^2}{n^2} \right)$$

taking $n \cdot \Delta t' = h$. In general an integral of the $k$th order becomes replaced by a summation of the same order in which the quantity summed is a $k$th order difference divided by $n^k$. The integrator circuit 38 has thus first of all to perform the appropriate division with respect to $n$ as in the first example. The similarity between this approach and that of the first example will be apparent but it must be stressed that they represent different and alternative methods according to the invention.

The function derived above and plotted in FIG. 4 and the function derived in the first example are both examples of interpolated functions of an original 0,0,1,0,0 function, which may be called a 'stab' function. It will be apparent that any more complex function composed of discrete values may be considered as a sum of a number of stab functions of respective different amplitudes. Correspondingly the interpolation of a more complex function may be achieved by the combination of a plurality of functions such as FIG. 4, each corresponding to one of those stab functions and with an appropriate peak amplitude.

Figure 5:
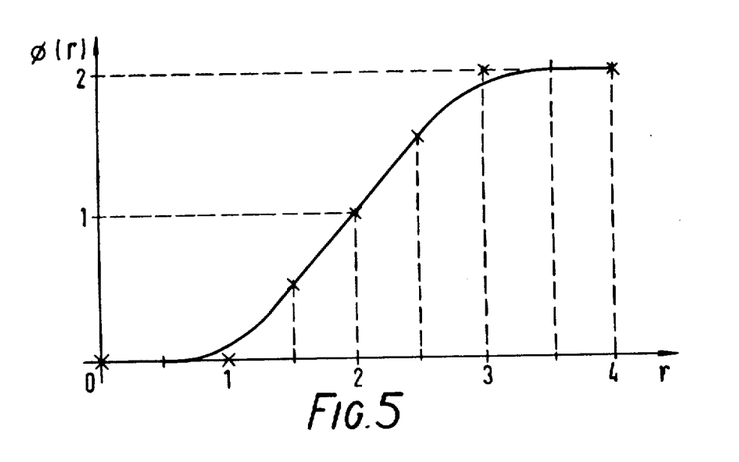

In practice, however, any more complex function is interpolated directly by a running summation as described above and not as a combination of stab functions. As a further example a function having values $f_1$, $f_2, f_3, f_4$, and $f_5$ of 0,0,1,2,2, respectively will be interpolated in $n=10$ steps per span by the method of the second example using the three expressions given. The interpolation function $\phi(r)$ thus obtained is shown plotted in FIG. 5. In the figure the plot is shown for illustration as a continuous curve through the derived values but as used the function has the calculated values given in the last column of the table. Accordingly the value corresponding to a value of $r$ most appropriate to matrix store address is the value used in the interpolation for that address. It will be seen that although passing through the first and last of the given set values, these values being denoted by X's in the figure, the curve of the interpolation does not necessarily pass through the remaining values, but assumes a smoothh form that at least lies close to them.

TABLE 2

| r | $f_k$ | $\Delta_k^1$ | $\frac{\Delta_1^1}{10}$ | $\frac{\Delta_2^1}{10}$ | $\frac{\Delta_3^1}{10}$ $\Delta_k^2$ | $\frac{\frac{1}{2} \cdot \Delta_1^2}{10^2}$ | $\frac{\frac{1}{2} \cdot \Delta_2^2}{10^2}$ | $\frac{\Delta_3^2}{10^2}$ | $\phi(r)$ |
|---|---|---|---|---|---|---|---|---|---|
| 0 | 0 | | | | | | | | 0 |
| 0.1 | | | 0 | | | | | | 0 |
| 0.2 | | | 0 | | | | | | 0 |
| 0.3 | | | 0 | | | | | | 0 |
| 0.4 | | | 0 | | | | | | 0 |
| 0.5 | | 0 | 0 | | | | | | 0 |
| 0.6 | | | 0 | | | .005 | | | 0.005 |
| 0.7 | | | 0 | | | .005 | | | 0.020 |
| 0.8 | | | 0 | | | .005 | | | 0.045 |
| 0.9 | | | 0 | | | .005 | | | 0.080 |
| 1 | | 0 | 0 | | 1 | .005 | | | 0.125 |
| 1.1 | | | 0 | | | .005 | | | 0.180 |
| 1.2 | | | 0 | | | .005 | | | 0.245 |
| 1.3 | | | 0 | | | .005 | | | 0.320 |
| 1.4 | | | 0 | | | .005 | | | 0.405 |
| 1.5 | | 1 | 0 | | | .005 | | | 0.500 |
| 1.6 | | | | 0.1 | | | 0 | | 0.6 |
| 1.7 | | | | 0.1 | | | 0 | | 0.7 |
| 1.8 | | | | 0.1 | | | 0 | | 0.8 |
| 1.9 | | | | 0.1 | | | 0 | | 0.9 |
| 2 | 1 | | | 0.1 | 0 | | 0 | | 1.0 |
| 2.1 | | | | 0.1 | | | 0 | | 1.1 |
| 2.2 | | | | 0.1 | | | 0 | | 1.2 |
| 2.3 | | | | 0.1 | | | 0 | | 1.3 |
| 2.4 | | | | 0.1 | | | 0 | | 1.4 |
| 2.5 | | 1 | | 0.1 | | | 0 | | 1.5 |
| 2.6 | | | | 0.1 | | | | −.005 | 1.595 |
| 2.7 | | | | 0.1 | | | | −.005 | 1.680 |
| 2.8 | | | | 0.1 | | | | −.005 | 1.755 |
| 2.9 | | | | 0.1 | | | | −.005 | 1.820 |
| 3 | 2 | | | 0.1 | −1 | | | −.005 | 1.875 |
| 3.1 | | | | 0.1 | | | | −.005 | 1.920 |
| 3.2 | | | | 0.1 | | | | −.005 | 1.955 |
| 3.3 | | | | 0.1 | | | | −.005 | 1.985 |
| 3.4 | | | | 0.1 | | | | −.005 | 1.995 |
| 3.5 | | 0 | | 0.1 | | | | −.005 | 2.000 |
| 3.6 | | | | | 0 | | | | 2 |
| 3.7 | | | | | 0 | | | | 2 |
| 3.8 | | | | | 0 | | | | 2 |
| 3.9 | | | | | 0 | | | | 2 |
| 4 | 2 | | | | 0 | | | | 2 |

In Table 2 the final column, giving values of the interpolation function $\phi(r)$, is formed according to a technique which may be illustrated with reference to the range $r=0.5$ to $r=1.5$ corresponding to the range $u=0$ to $u=1$. For convenience $$\Delta_1^2/n^2$$

is denoted by $\alpha$, and $$\left( \sum_{0}^{u} \sum_{0}^{i} \frac{\Delta_1^2}{n^2} \right) \text{ by } S_u,$$

with $n$ having the value 10, so that in fact $\alpha$ has the valuue 0.01. It is evident that $$S_u = \frac{1}{2} u^2 \alpha,$$

and that correspondingly $$S_{u+1} = \frac{1}{2}(u^2 + 2u + 1)\alpha$$

$$= S_u + u\alpha + \frac{1}{2}\alpha.$$

It follows that the first order difference $$\Delta_{S_u}^1 = u\alpha + \frac{1}{2}\alpha,$$

and that the second order difference $$\Delta_{S_u}^2 = \alpha.$$

More particularly it follows that $$\Delta_{S_{u+1}}^1 = (u+1)\alpha + \frac{1}{2}\alpha$$

$$= \Delta_{S_u}^1 + \Delta_{S_u}^2.$$

This recurrence formula together with the recurrence formula $$S_{u+1} = S_u + \Delta_{S_u}^1$$

is used to construct the final column of Table 2 on the basis of running summation.

At the outset, that is to say for $u=0$, it is given that $$S_0 = 0,$$

$$\Delta^1 S_0 = \frac{1}{2}\alpha,$$

$$\Delta^2 S_0 = \alpha.$$

The final column of Table 2 thus builds up in accordance with the details of Table 3.

TABLE 3

| $\mu$ | $\Delta^2 S_\mu$ | $\Delta^1 S_\mu$ | $S_\mu$ |
|---|---|---|---|
| 0 | $\alpha$ | $1/2\alpha$ | 0 |
| 1 | $\alpha$ | $1/2\alpha+\alpha=3/2\alpha$ | $0+1/2\alpha=1/2\alpha$ |
| 2 | $\alpha$ | $3/2\alpha+\alpha=5/2\alpha$ | $1/2\alpha+3/2\alpha=2\alpha$ |
| 3 | $\alpha$ | $5/2\alpha+\alpha=7/2\alpha$ | $2\alpha+5/2\alpha=9/2\alpha$ |

TABLE 3-continued

| $\mu$ | $\Delta^2 S_\mu$ | $\Delta^1 S_\mu$ | $S_\mu$ |
|---|---|---|---|
| 4 | $\alpha$ | $7/2\alpha + \alpha = 9/2\alpha$ | $9/2\alpha + 7/2\alpha = 8\alpha$ |

It is to be noted that the value of $\alpha$ having been obtained by division with respect to $n$ in the first place, as mentioned, the value $\frac{1}{2}\alpha$ appearing in the top of the third column of Table 2 can be derived simply by the shift of one digit place in the register, if $\alpha$ is in binary digital form. Thereafter the third column is built solely by a running summation, and a running summation suffices to construct the whole of the forth column giving the values of $S_u$. The step-by-step integration of the invention is thus accomplished in these terms in relation to Table 2 by utilising two accumulators.

The procedure given above using first and second order differences may be adapted to avoid the one-digit shift at the commencemment of Table 3 so as to form the value $\frac{1}{2}\alpha$. The adapted procedure, which is set out in Table 4 works entirely in multiples of $\alpha$, while yielding an interpolation function differing but very slightly from that calculated in accordance with Table 3. In Table 4 the interpolation function, given in the column headed S, is formulated at mid-points of the subspans in a manner similar to the first example above. The values of $\Delta^1 S_u$ in Table 3 are replaced by values decreased by the extent $\frac{1}{2}\alpha$, as shown in the column of Table 4 under the heading $\Delta^1 S$. Second order difference values are taken as before, as shown in the column designated $\Delta^2 S$ in Table 4, although positioned in the column as mid-subspan values. The processing apart from the simplification that there is no initial one-digit shift is otherwise the same.

TABLE 4

| $\mu$ | $\Delta^2 S$ | $\Delta^1 S$ | S |
|---|---|---|---|
| 0 |  | 0 | 0 |
|  | $\alpha$ |  |  |
| 1 |  | $0+\alpha=\alpha$ |  |
|  | $\alpha$ |  | $0+\alpha=\alpha$ |
| 2 |  | $\alpha+\alpha=2\alpha$ |  |
|  | $\alpha$ |  | $\alpha+2\alpha=3\alpha$ |
| 3 |  | $2\alpha+\alpha=3\alpha$ |  |
|  | $\alpha$ |  | $3\alpha+3\alpha=6\alpha$ |
| 4 |  | $3\alpha+\alpha=4\alpha$ |  |

The manner of interpolation used to illustrate the invention may be termed quadratic, since the highest order component of variation present in the interpolation function in such illustration is that due to second order integration, namely that corresponding to the continuous integration form $$\iint \frac{1}{h^2} dt' dt.$$

A greater measure of accuracy of interpolation with improved smoothing of statistical fluctuations may be achieved by superposing on the process described a component of third order integration. This superposed integration is of identical step-by-step character, and is such that throughout the $k$th span, for all $k$ for which order difference is defined, the summation corresponds to the continuous integration expressed by $$\iiint \frac{1}{h^3} dt'' dt' dt.$$

The invention may be extended on these lines to higher order of integration is desired.

It has been observed that the derived interpolated function runs smoothly through the points of the original function, not necessarily passing through any value which is not repeated a sufficient number of times. It is desired that the interpolated function should reliably start and end on exact values that may be arranged by preceding the first point and following the final point by similar values so that they are repeated a number of times at least equal to the number of recurrent addition processes used. Thus if a function is to reliably start at and return to zero it can, for an interpolation using second order differences, be preceded by two zeros and followed by two zeros.

Although the invention has been described in terms of absorption data processed by a convolution method, it is applicable to any processing method requiring interpolation between a limited number of derived data.

What I claim is:

1. A method of constructing a representation of the distribution of absorption in a planar region of a body including the steps of providing data signals representing the absorption of the radiation along a plurality of substantially parallel paths in the plane of the said region, interpolating between the said data signals to provide further data signals representing the absorption of the radiation along an increased number of such paths and allocating, to each of a plurality of predetermined points in a field notionally delineated in the said region, the data signal or further data signal associated with the path whose centreline passes closest to that point, wherein the interpolation is achieved by forming signals representing difference of said data extending to order $m$, where $m$ is at least two, subdividing some of said difference signals and combining the subdivided differences by running addition.

2. A method according to claim 1 wherein the interpolation is based soley on the combination of subdivided differences of order $m$.

3. A method according to claim 1 wherein $m$ has the value 2.

4. A method to claim 1 wherein $n$ subdivided values are provided for each $m^{th}$ order difference value to be so subdivided, each being equal to the respective difference divided by $n^m$.

5. An apparatus for constructing a representation of the distribution of absorption in a planar region of a body including means for providing data signals representing the absorption of the radiation along a plurality of substantially parallel paths in the plane of the said region, means for forming signals representing differences of said data extending to order $m$, where $m$ is at least two, means for subdividing some of said difference signals and combining the subdivided differences by running addition to provide further data signals representing the absorption of the radiation along an increased number of paths, storage means having a plurality of locations associated with a plurality of predetermined points in a field notionally delineated in the said region and means for allocating of each of said locations the data signal or further data signal associated with path whose centreline passes closest to the point associated with that location.

* * * * *